United States Patent [19]
Rapp et al.

[11] Patent Number: 5,649,548
[45] Date of Patent: Jul. 22, 1997

[54] TRANSDUCER FOR MONITORING LABOR PAINS

[75] Inventors: Jurgen Rapp, Villingen-Schwenningen; Fritz Stepper, Boeblingen; Andreas Maurer, Stuttgart, all of Germany

[73] Assignee: Hewlett-Packard Company, Palo Alto, Calif.

[21] Appl. No.: 388,811

[22] Filed: Feb. 15, 1995

[30] Foreign Application Priority Data

Mar. 12, 1994 [DE] Germany ................ 44 08 409.9

[51] Int. Cl.⁶ .................................................. A61B 5/03
[52] U.S. Cl. ........................................................ 128/775
[58] Field of Search ............................. 128/774, 775, 128/778, 782

[56] References Cited

U.S. PATENT DOCUMENTS

| | | | |
|---|---|---|---|
| 4,640,295 | 2/1987 | Isaacson | 128/775 |
| 4,873,986 | 10/1989 | Wallace | 128/775 |
| 4,944,307 | 7/1990 | Hon et al. | 128/775 |
| 5,184,619 | 2/1993 | Austin | 128/775 |

FOREIGN PATENT DOCUMENTS

| | | | |
|---|---|---|---|
| 0275397 | 1/1990 | Germany | 128/775 |
| 0003115 | 6/1986 | WIPO | 128/775 |

*Primary Examiner*—Max Hindenburg

[57] ABSTRACT

Watertight transducer for measuring the contraction of the uterus with a transducer casing, wich has on its underside a diaphragm made from a soft material, such as e.g. elastomeric plastic. The transfer of the uterine contractions takes place from the diaphragm for a ram to a dynamometer. The interior of the transducer is vented by means of a ventilating hose, whose opening to the external air is remote from the transducer, in order to avoid measuring errors as a result of temperature fluctuations.

9 Claims, 3 Drawing Sheets

TRANSDUCER FOR MONITORING LABOR PAINS

FIELD OF THE INVENTION

The invention relates to a transducer for monitoring labour pains during pregnancy having a transducer casing connectable by means of a cable to a monitoring device, a ram movable in its axial direction and a dynamometer in the transducer casing, the ram transferring the labour pains to the dynamometer for conversion into electric signals.

BACKGROUND OF THE INVENTION

In gynecology and obstetrics it is known to determine the uterine activity by means of a tocometer, which measures the contraction of the uterus and transmits it to a monitoring device, which records the time behaviour of the labour pain intensity by means of a recorder. Measurement of the contractions takes place by means of a dynamometer, e.g. a bender bar with a strain gauge and which is operated by means of a ram movable in its axial direction.

In conventional transducers the ram is guided in the underside of the transducer and projects from the transducer casing, so that its end face comes to rest on the abdominal wall of the pregnant woman. Thus, the uterine activity can be directly recorded through the axial mobility of the ram and transmitted to the dynamometer. As in the medical field transducers must be easily cleanable and disinfectable, it should have no depressions, grooves or difficultly accessible points on the casing. However, in the known construction the space between the end face of the ram and the underside of the transducer is difficultly accessible for cleaning purposes. In addition, the transducer must be as watertight as possible, so that on the one hand no disinfectant can enter it and on the other it is also possible to use the transducer under water. This condition is inadequately fulfilled in the known transducers, because the passage of the ram through the underside of the transducer casing represents a location for possible leaks.

The problem of the present invention is therefore to improve the known transducer in such a way that it can also be used under water.

SUMMARY OF THE INVENTION

This problem is solved by a transducer having the features of the main claim. For this purpose the ram is located in the interior of the transducer casing and the underside of the latter used for performing the measurements has a diaphragm, which moves the ram as a function of the labour pains. Thus, there is a high degree of sealing of the transducer, because the ram recording the uterine activity no longer has to be guided through the underside of the transducer casing. Therefore the uterine activity is firstly transferred to the diaphragm, which must consequently be made from a soft material, e.g. elastomeric plastic. In addition, for the venting or ventilating of the interior of the transducer casing there is an opening which is remote from said casing. This serves to compensate pressure changes in the interior of the transducer casing resulting from the expansion or contraction of the enclosed air volume due to temperature changes.

During the measurement the transducer, which is roughly at ambient temperature, is applied to the warm abdomen of the pregnant woman. The transducer slowly becomes warmer, so that the air in the interior expands, the pressure rises and the diaphragm is pressed away from the ram if no pressure compensation takes place. An additional force must then be applied by the abdomen, which overcomes the increased internal pressure on the diaphragm due to the greater heating action. Both this heating and also a cooling, during which the diaphragm is no longer correctly in contact with the abdominal wall, would lead to measurement errors, If there was no corresponding compensation possibility for the interior of the transducer casing.

In order that the watertightness is ensured, it is necessary for the opening, by means of which air can pass into or out of the interior, is so far removed from the transducer casing, that also when the transucer is used under water no moisture can penetrate the interior. This can e.g. be brought about by means of a separate ventilating hose connected to the interior of the transducer casing or by means of the in any case present connecting cable for the transmission of signals to the monitoring device.

Further advantageous developments can be gathered from the subclaims.

In the case of a separate ventilating hose, the latter can either be remote from the cable or can be connected thereto. One possibility is to fix the ventilating hose externally to the cable, or produce it with the cable jacket.

In a preferred embodiment the ventilating hose is in the cable interior. The end of the ventilating hose can either be passed out of the cable interior in the vicinity of the plug and therefore sufficiently far from the transducer or, according to an advantageous development, can end in the cable plug. In this variant the hose can be passed through the opening of an unused plug pin, which offers the additional advantage that the hose opening is protected and cannot be as rapidly blocked by contamination. In the vicinity of the transducer the ventilating hose with the connecting wires for the dynamometer is passed through a corresponding sealed opening in the transducer casing.

According to another advantageous development the ventilation of the interior can take place by means of the cable used in the cavity between the cable conductors and which has a cable ventilating opening remote from the transducer casing. Once again ventilation can either take place by means of a missing plug pin or by means of an additional opening in the cable jacket.

Thus, it is possible with the transducer according to the invention to also perform under water faultless measurements, because the transducer casing can be constructed in watertight manner and changes in the atmosperic pressure within the transducer casing due to temperature fluctuations can be compensated by a ventilating opening positioned remotely from the transducer casing.

DESCRIPTION OF THE DRAWINGS

The invention is described in greater detail hereinafter relative to non-limitative embodiments and the attached drawings, wherein show.

DETAILED DESCRIPTION OF EMBODIMENTS

Figure 1:
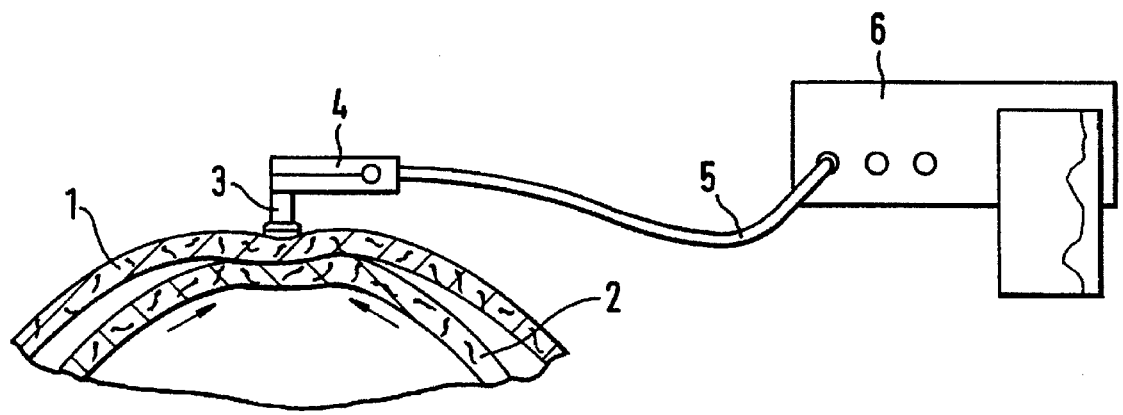
FIG. 1 A diagrammatic representation of the measuring principle.

FIG. 1 shows the principle of tocometry on the abdominal cavity 1, under which is located the uterus 2, which contracts in the direction of the arrow. On the abdominal wall 1 is placed a ram 3, which records the force through the uterine contraction and transmits it to a dynamometer 4. The signals converted by the dynamometer 4 are transmitted by means of a cable 5 to a monitoring device 6 having a recorder.

Figure 2:
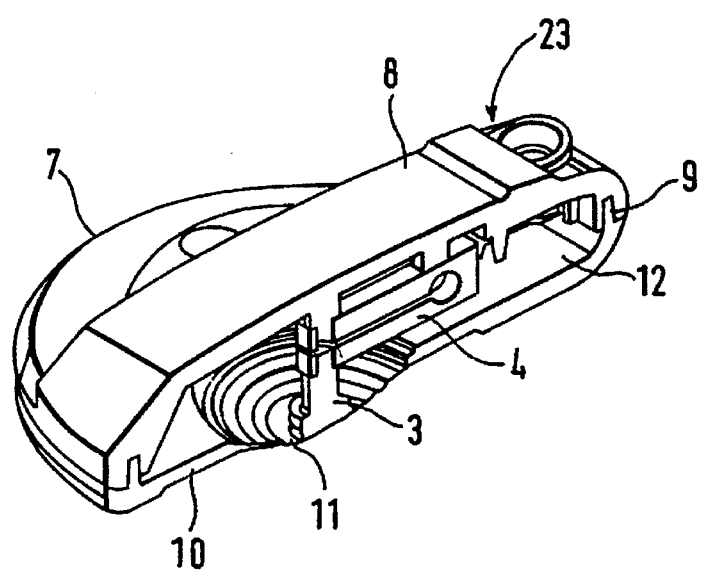
FIG. 2 A perspective sectional representation of a transducer.

FIG. 2 shows a transducer 7 for recording the measured values for the monitoring device 6, which has a transducer casing 8, which is given a watertight construction by means of an allround seal 9. The underside 10 of the transducer casing 8, which is placed on the abdominal wall 1, has a soft diaphragm 11 made from an elastomeric plastic. On said diaphragm 11 is placed the ram 3, which is connected to the dynamometer 4. The complete interior 12 of the transducer casing 8 is sealed against the penetration of water and makes available a specific air volume. The connection of the cable 5 takes place by means of the opening 23.

Figure 3:
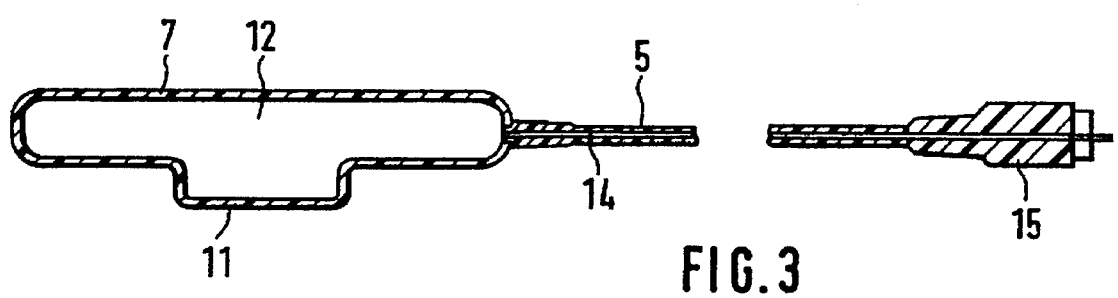
FIG. 3 A diagrammatic representation of a transducer with a ventilating hose in the cable.

As shown in FIG. 3, for compensating the air volume due to temperature fluctuations, in the interior of the cable is provided a ventilating hose 14, which at one end with the cable bushing 13 passes into the interior 12 of the transducer casing 8. At the other end the ventilating hose 14 is guided in the cable plug and terminates in the vicinity of the socket of said plug. Therefore there is a ventilation possibility for the interior 12 as a result of said ventilating hose 14 and simultaneously there is no risk of water or the like passing into the interior 12 of the transducer 7.

Figure 4:
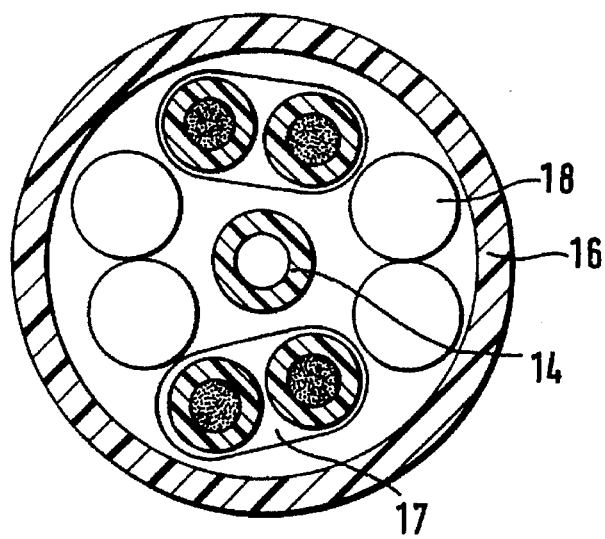
FIG. 4 A cross-section through a cable with ventilating hose.

FIG. 4 shows in section a cable 5 with the cable jacket 16, screened conductors 17, filling material 18 and the ventilating hose 14. In order to ensure a reliable connection of the enclosed air volume with the external air, during cable manufacture a thin Teflon tube with an internal diameter of approximately 0.9 mm and an external diameter of approximately 1.5 mm is also processed therewith. The ventilating hose 14 can run concentrically or eccentrically in the cable 5, which can contain one or more conductors 17.

Figure 5A:
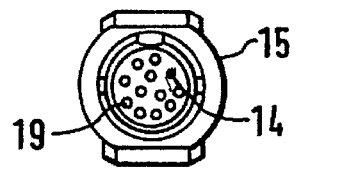
FIG. 5a A front view of the plug showing the ventilation hose outlet.
Figure 5B:
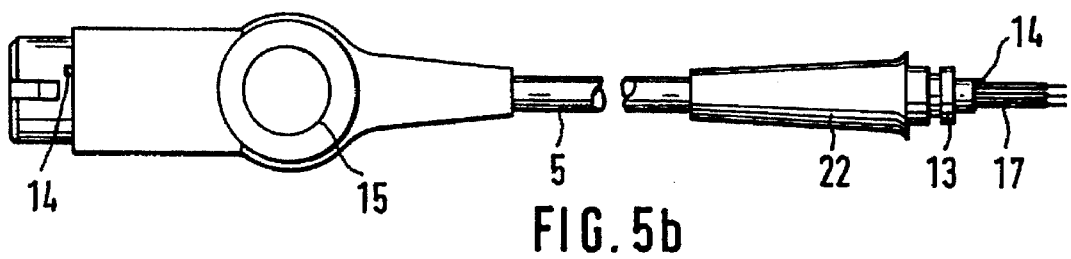
FIG. 5b A top view of the cable with the cable plug and the end of the ventilation hose at one end and the cable bushing with conductors and ventilating hoses at the other end.

FIG. 5a is a front view of the plug with the contact pins 19 and the end of the ventilating hose 14. FIG. 5b shows the cable 5 in a technical embodiment with the cable plug 15 and the end of the ventilating hose 14 at one end, as well as the cable bushing 13 and the led out conductors 17 and ventilating hose 14 at the other end. Both ends of the cable 5 are moulded, a cable sleeve 22 being moulded onto the side which is introduced into the transducer 7. The ventilating hose 14 projects a few millimeters out of the cable end and into the transducer 7. At the other side the cable plug 15 is moulded on and the ventilating hose 14 is led out through a suitable opening. It is also possible to create a connection between the ventilating hose 14 and the external air by an opening in the cable plug 15. In the example shown in FIG. 5 the ventilating hose 14 is passed through the opening of an unused contact pin 19, which reduces the risk of contamination or dirtying of the hose opening. The contact pin is omitted.

Figure 6:
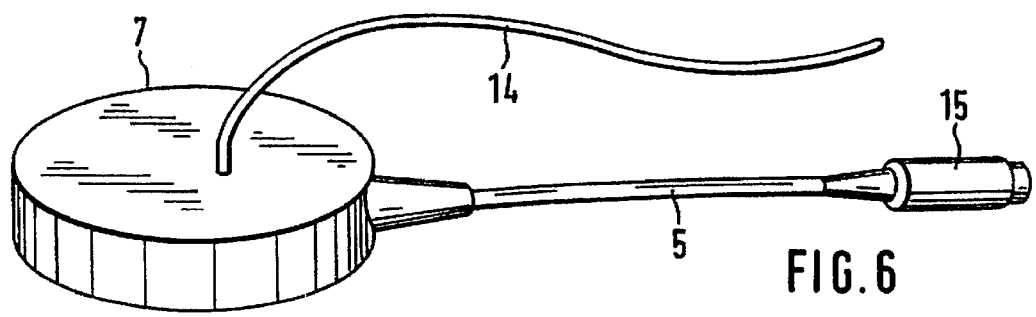
FIG. 6 A diagrammatic representation with a separate ventilating hose guide.

FIG. 6 diagrammatically shows an embodiment in which the ventilating hose 14 is separate from the cable 5.

Figure 7A:
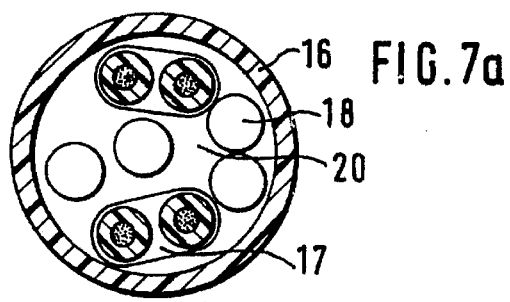
FIG. 7a A cross-section through a cable with a cavity used for ventilating.
Figure 7B:
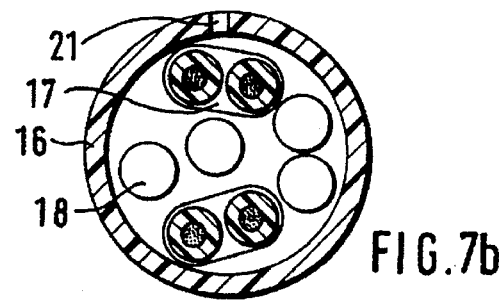
FIG. 7b A cross-section through a cable with a cable ventilation opening in the cable jacket.

FIG. 7a shows the cross-section through a cable 5 with the cable jacket 16, screened conductors 17 and filling material 18, in which the cavity 20 is used for ventilating the interior 12 of the transducer 7. FIG. 7b shows the cable of FIG. 7a with a cable ventilation opening 21 in the cable jacket 16, which is to be installed as far away as possible from the transducer 7, so as to ensure that no water or the like can pass into the cavity 20 and therefore into the interior 12.

Figure 8A:
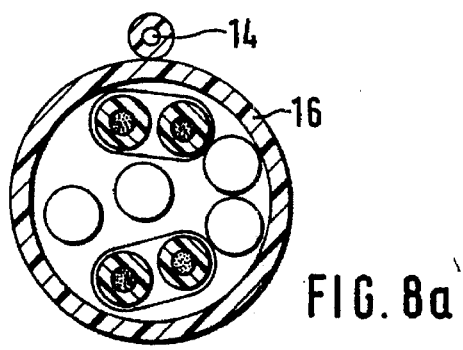
FIG. 8a Another embodiment with a ventilating hose bonded together with the cable.
Figure 8B:
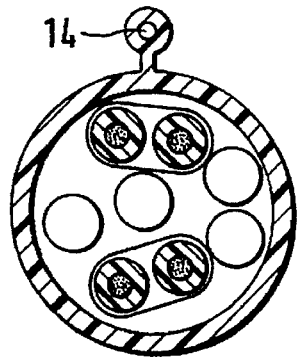
FIG. 8b An embodiment with a ventilating hose extruded together with the cable jacket.

FIGS. 8a and 8b show two embodiments with a ventilating hose 14, which can either be bonded together with the cable (FIG. 8a), or extruded together with the cable jacket 16 (FIG. 8b).

Figure 9A:
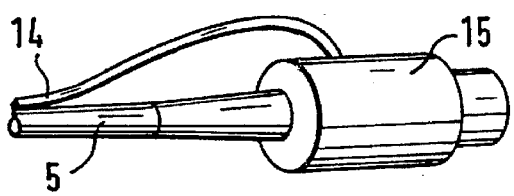
FIG. 9a An embodiment with a separate ventilating hose guided in the cable plug.
Figure 9B:
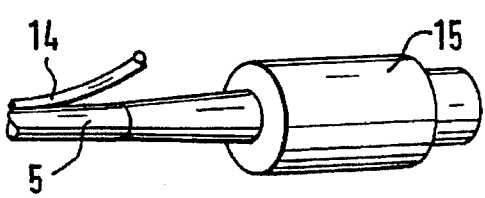
FIG. 9b An embodiment with a separate ventilating hose which terminates in the vicinity of the cable plug.

FIG. 9 shows the passage of a separate ventilating hose 14 in the vicinity of the cable plug 15. According to FIG. 9a the ventilating hose 14 is guided in the cable plug and connected therein, in the manner described hereinbefore. According to FIG. 9b the ventilating hose 14 terminates in the open in the vicinity of the cable plug 15.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Transducer for monitoring labor pains during pregnancy with a transducer casing connectable by means of a cable plug and cable to a monitoring device, a ram movable in its axial direction within the transducer casing, a dynamometer in the transducer casing, the ram contacting the dynamometer for transmitting the labor pains to the dynamometer for conversion into electrical signals, wherein an underside of the transducer used for taking the measurements comprises a diaphragm whose inside engages the ram and transmits the labor pains directly to said dynamometer, said transducer casing provided with an opening to the environment which is remote from the transducer casing for venting and/or ventilating the interior of said transducer casing.

2. Transducer according to claim 1, wherein the diaphragm is made from an elastomeric plastic.

3. Transducer according to claim 1, wherein a ventilating hose is connected to the transducer casing.

4. Transducer according to claim 3, wherein the ventilating hose is connected to the cable.

5. Transducer according to claim 3, wherein the ventilating hose is in the interior of the cable.

6. Transducer according to claim 3, wherein the ventilating hose terminates in the cable plug.

7. Transducer according to claim 1, wherein the venting and ventilating of the interior takes place by means of the cavity of the cable, the cavity having a cable ventilating opening remote from the transducer casing.

8. Transducer according to claim 7, wherein the cable ventilating opening is located in the cable jacket.

9. Transducer according to claim 7, wherein the cable ventilating opening is located in the end face of the cable plug.

* * * * *